United States Patent
Mewshaw et al.

(10) Patent No.: US 6,313,114 B1
(45) Date of Patent: Nov. 6, 2001

(54) 3,4-DIHYDRO-2H-BENZO[1,4]OXAZINYL-METHYL)-[3-(1H-INDOL-3YL)-ALKYL]-AMINES

(75) Inventors: Richard E. Mewshaw, King of Prussia, PA (US); Dahui Zhou, East Brunswick; Ping Zhou, Plainsboro, both of NJ (US)

(73) Assignee: American Home Products Corp, Madison, NJ (US)

( * ) Notice: Subject to any disclaimer, the term of this patent is extended or adjusted under 35 U.S.C. 154(b) by 0 days.

(21) Appl. No.: 09/475,940

(22) Filed: Dec. 30, 1999

Related U.S. Application Data

(60) Provisional application No. 60/126,412, filed on Jan. 7, 1999, now abandoned.

(51) Int. Cl.⁷ ............... C07D 413/12; A61K 31/538
(52) U.S. Cl. ............................. 514/230.5; 544/105
(58) Field of Search .................... 514/230.5; 544/105

(56) References Cited

U.S. PATENT DOCUMENTS

| | | | |
|---|---|---|---|
| 3,717,634 | 2/1973 | Wu et al. | 260/256.4 |
| 4,612,312 | 9/1986 | Hibert et al. | 514/225 |
| 5,106,849 | 4/1992 | Abou-Gharbia | 514/247 |
| 5,278,160 | 1/1994 | Abou-Gharbia et al. | 514/247 |
| 5,482,940 | 1/1996 | Abou-Gharbia et al. | 514/252 |

FOREIGN PATENT DOCUMENTS

WO8907596-A  8/1989  (WO).

OTHER PUBLICATIONS

Le Poul et al., *Arch. Pharmacol*, 352:141 (1995).
Artigas et al., *Trends Neurosci.*, 19:378–383 (1996).

*Primary Examiner*—John M. Ford
(74) *Attorney, Agent, or Firm*—Joseph M. Mazzarese

(57) ABSTRACT

Compounds are provided which have the following formula:

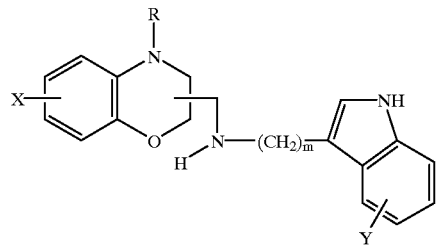

wherein:
- R is hydrogen, alkyl of 1 to 6 carbon atoms, phenyl, or substituted phenyl;
- X and Y are each, independently, hydrogen, halogen, cyano, or alkoxy of 1 to 6 carbon atoms; and
- m is 1 to 5; or
- a pharmaceutically acceptable salt thereof.

23 Claims, No Drawings

3,4-DIHYDRO-2H-BENZO[1,4]OXAZINYL-METHYL)-[3-(1H-INDOL-3YL)-ALKYL]-AMINES

CROSS REFERENCE TO RELATED APPLICATIONS

This application claims the benefit of U.S. Provisional Application No. 60/126,412, which was converted from U.S. patent application Ser. No. 09/226,831 filed Jan. 7, 1999 now abandoned.

FIELD OF INVENTION

This invention is directed to compounds useful in the treatment of neurological diseases caused by disorders of the serotonin-affected neurological systems. More specifically, the present invention is directed to compounds useful as anxiolytic and/or antidepressant agents.

BACKGROUND OF INVENTION

Pharmaceuticals which enhance the neurotransmission of serotonin (5-HT) are useful for the treatment of many psychiatric disorders, including depression and anxiety. The first generation of non-selective serotonin-affecting drugs operated through a variety of physiological means which caused them to possess numerous undesired side-effects. The more recently prescribed drugs, the selective serotonin reuptake inhibitors (SSRIs), act predominately by inhibiting 5-HT, which is released at the synapses, from being actively removed from the synaptic cleft via a presynaptic serotonin transport carrier. Since SSRIs require several weeks before they exert their full therapeutic effect, this 5-HT blockade mechanism cannot fully account for their therapeutic activity. It is speculated that this two week induction which occurs before a full antidepressant effect is observed, is due to the involvement of the 5-HT1A autoreceptors which suppress the firing activity of 5-HT neurons, causing a dampening of the therapeutic effect. Studies suggest that after several weeks of SSRI administration, a desensitization of the 5-HT autoreceptors occurs allowing a full antidepressant effect in most patients. (See, e.g., Le Poul et al., *Arch. Pharmacol.*, 352:141 (1995)). Hence, it is believed that overriding this negative feedback by using 5HT1A antagonists would potentially increase and accelerate the clinical antidepressant response. Recent studies by Artigas et al., *Trends Neurosci.*, 19:378–383 (1996), suggest a combination of 5-HT1A activity and inhibition of 5-HT uptake within a single molecular entity can achieve a more robust and fast-acting antidepressant effect.

The present invention relates to a new class of molecules which have the ability to act at the 5-HT1A autoreceptors and concommitantly with the 5-HT transporter. Such compounds are therefore potentially useful for the treatment of depression as well as other serotonin disorders.

Compounds having antidepressant and anxiolytic activity due to their affinity for the 5HT1A autoreceptors are disclosed in, e.g., U.S. Pat. No. 3,717,634 which claims N-(heteroarcyclic)-piperazinylalkyl derivatives of aza-spiroalkanediones Aryl and heteroaryl piperazinylalkyl carboxamides having 5HT1A activity are disclosed, e.g., in U.S. Pat. Nos. 5,106,849; 5,278,160; and 5,482,940.

Glutarimide derivatives having anxiolytic and antihypertensive activity are disclosed in U.S. Pat. No. 4,612,312.

Benzoxazine and thiazine derivatives useful for treating psychotic disorders and schizophrenia are disclosed in PCT Patent Application Publication No. WO 8907596-A.

However, none of these patents disclose compounds which act at both the 5HT1A autoreceptors and the 5-HT-transporter.

SUMMARY OF INVENTION

The present invention is directed to compounds which are both active towards $5HT_{1A}$ receptors and inhibit 5HT transport. Such compounds are useful in treating disorders relating to serotinin concentrations, such as anxiety and depression.

The present invention is directed to compounds of the formula:

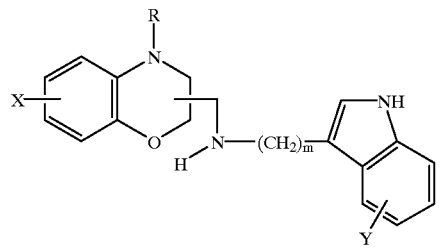

wherein:

R is hydrogen, alkyl of 1 to 6 carbon atoms, phenyl, benzyl or substituted phenyl;

X and Y are each, independently, hydrogen, halogen, cyano, or alkoxy of 1 to 6 carbon atoms; and m is 1 to 5;or a pharmaceutically acceptable salt thereof.

The present invention is further directed to methods for alleviating the symptoms of depression comprising administering to a patient in need thereof an antidepressant effective amount of a compound represented by the following formula:

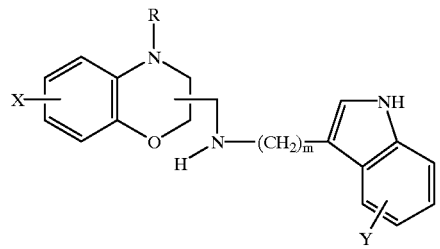

wherein:

R is hydrogen, alkyl of 1 to 6 carbon atoms, phenyl, benzyl, or substituted phenyl;

X and Y are each, independently, hydrogen, halogen, cyano, or alkoxy of 1 to 6 carbon atoms; and m is 1 to 5;or a pharmaceutically acceptable salt thereof.

DETAILED DESCRIPTION OF THE INVENTION

Preferably, the present compounds are those represented by the formula set forth above wherein:

R is hydrogen or alkyl of 1 to 4 carbon atoms;

X and Y are each, independently, hydrogen, halogen or cyano; and m is 2 to 4; or a pharmaceutically acceptable salt thereof.

Most preferably, the compounds of the present invention include:

(3,4)-Dihydro-2H-benzo[1,4]oxazine-2-yl-methyl)-[3-(1H-indo-3-yl)-propyl]-amine;

[3-(1H-Indol-3-yl)-propyl]-(4-methyl-3,4-dihydro-2H-benzo[1,4]oxazin-2-yl-methyl)-amine;

(4-Benzyl-3,4-dihydro-2H-benzo[1,4]oxazin-2-yl-methyl)-[3-(1H-indo-3-yl)-propyl]-amine;

(4-Benzyl-3,4-dihydro-2H-benzo[1,4]oxazin-2-yl-methyl)-[3-(1H-indo-3-yl)-butyl]-amine;

[3-(5-Fluoro- 1H-indol-3-yl)-propyl]-(4-methyl-3,4-dihydro-2H-benzo[1,4]oxazin-2yl-methyl)-amine;

[3-(1H-Indol-3-yl)-propyl]-(4-benzyl-3,4-dihydro-2H-benzol[1,4]oxazin-2-yl-methyl)-amine;

[3-(1H-Indol-3-yl)-propyl]-(4-phenyl-3,4-dihydro-2H-benzo[1,4]oxazin-2-yl-methyl)-amine;

[3-(5-Fluoro-1H-indol-3-yl)-propyl]-(4-isopropyl-3,4-dihydro-2H-benzo[1,4]oxazin-2-yl-methyl)-amine;

[3-(1H-Indol-3-yl)-butyl]-(4-isopropyl-3,4-dihydro-2H-benzo[1,4]oxazin-2-yl-methyl)-amine;

[3-(5-Fluoro-1H-indol-3-yl)-propyl]-(4-isobutyl-3,4-dihydro-2H-benzo[1,4]oxazin-2-yl-methyl)-amine;

[3-(5-Fluoro-1H-indol-3-yl)-propyl]-(4-phenyl-3,4-dihydro-2H-benzo[1,4]oxazine-2-yl-methyl)-amine;

[3-(5-Fluoro-1H-indol-3-yl)-butyl]-(4-phenyl-3,4-dihydro-2H-benzo[1,4]oxazine-2-yl-methyl)-amine;

[3-(5-Fluoro-1H-indol-3-yl)-propyl]-(4-ethyl-3,4-dihydro-2H-benzo[1,4]oxazin-2-yl-methyl)-amine;

[3-(5-Fluoro-1H-indol-3-yl)-propyl]-(4-propyl-3,4-dihydro-2H-benzo[1,4]oxazine-2-yl-methyl)-amine;

(7-Chloro-4-methyl-3,4-dehydro-2H-benzo[1,4]oxazin-2-yl-methyl)-[3-5-fluoro-1H-indol-3-yl)-propyl]-propyl-amine;

(3,4-Dihydro-2H-benzo[1,4]oxazin-2-yl-methyl)-[3-(5-fluoro-1H-indol-3-yl)-propyl-amine;

(7-Methoxy-3,4-dihydro-2H-benzo[1,4]oxazin-2-yl-methyl)-[3-(5-fluoro-1H-indol-3-yl)-propyl]-amine;

[3-(5-Fluoro-1H-indol-3-yl)-propyl]-(4-phenyl-3,4-dihydro-2H-benzo[1,4]oxazin-2-yl-methyl)-amine; and (3,4-dihydro-2H-benzo[1,4]oxazin-3-yl-methyl)-[3(5-fluoro-1H-indol-3-yl)propyl]-amine.

As used herein, the terms "alkyl" and "alkoxy" are meant to include both straight and branched carbon chains. The term "halogen" is meant to include fluorine, chlorine, bromine and iodine. The term "substituted phenyl" is meant to include a phenyl moiety substituted with an alky, a halogen, or alkoxy group.

The pharmaceutically acceptable salts of the present compounds are those derived from such inorganic cations such as sodium, potassium and the like; organic bases, such as mono-, di- and trialkyl amines of 1 to 6 carbon atoms, per alkyl group and mono-, di- and trihydroxyalkyl amines of 1–6 carbon atoms per alkyl group; and organic and inorganic acids, such as acetic, lactic, citric, tartaric, succinic, maleic, malonic, gluconic, hydrochloric, hydrobromic, phosphoric, nitric, sulfuric, methane sulfonic, and similarly known acceptable acids.

The compounds of the present invention may be prepared by any suitable method as will be recognized by one skilled in the art. However, the present compounds may be advantageously prepared according to any one of Schemes 1, 2, 3, or 4 set forth below.

Scheme 1

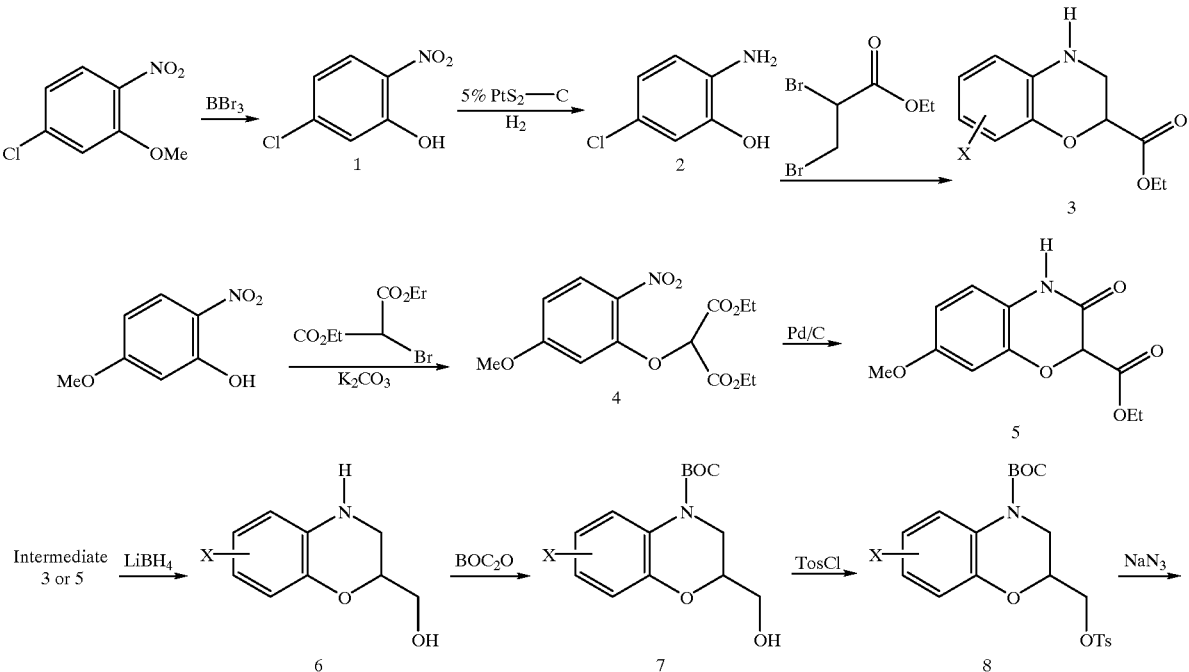

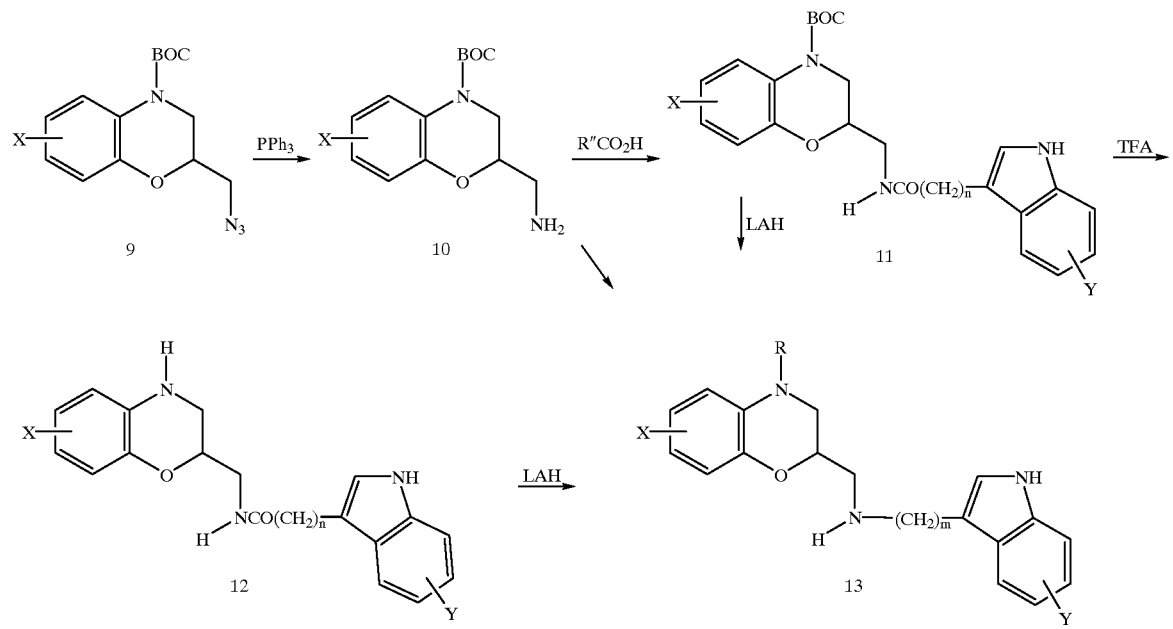
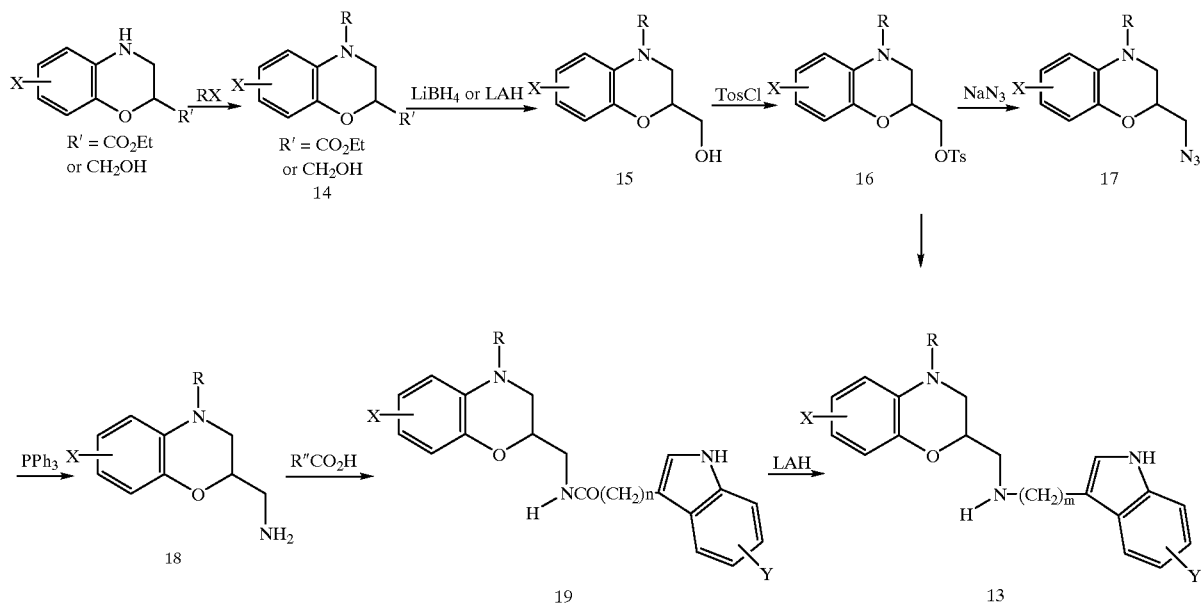

Scheme 3

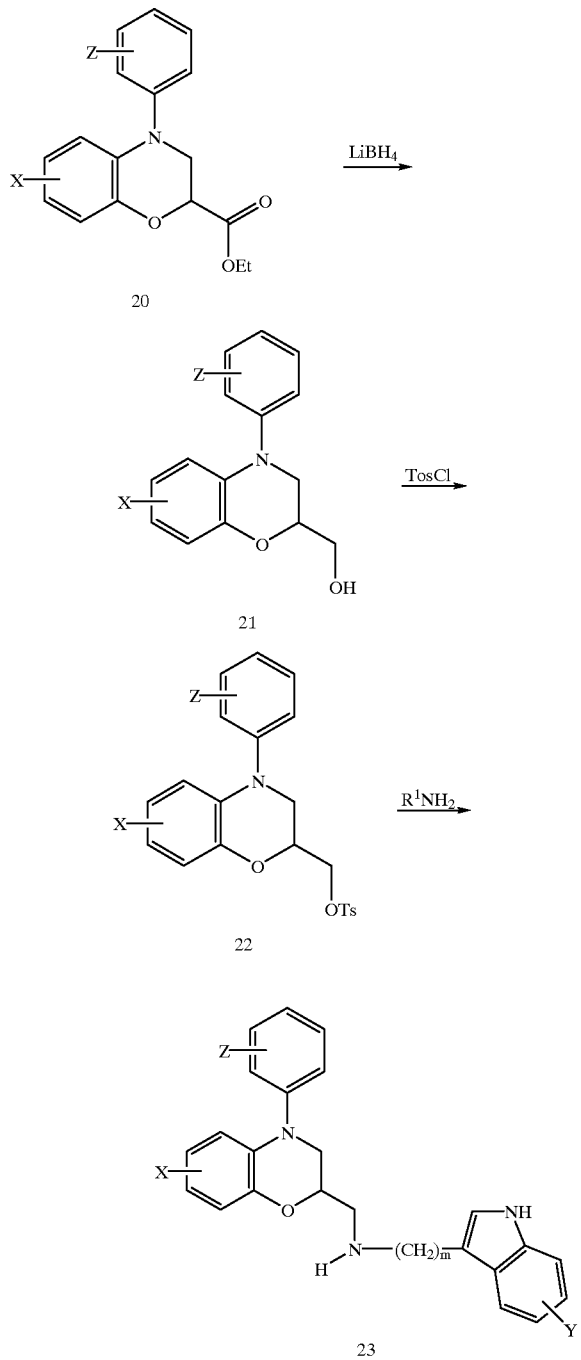

Scheme 4

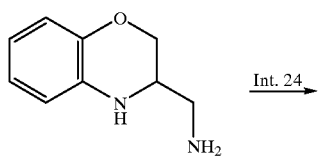

In Schemes 1 to 4,

R may be methyl, ethyl, propyl, isopropyl or isobutyl;

R' may be $CO_2Et$ or $CH_2OH$;

R" may be 3-indolyl-propyl or 3-indolyl-butyl;

X may be hydrogen, chlorine or methoxy;

Y may be hydrogen or fluorine;

Z may be hydrogen;

n is 2 or 3; and m is 3 or 4.

Specific exemplification of the production of representative compounds of this invention is given in the following procedures.

INTERMEDIATE 1

2Nitro-5-chloro-phenol

To a solution of 5-chloro-2-nitroanisole (10 g, 53 mmol) in methylene chloride (30 mL) was added 1 M boron tribromide (11 mL, 0.11 mol) at −78° C. The reaction mixture was stirred for 3 hours and allowed to warm to room temperature while stirring for another 12 hours. The reaction was quenched by the cautious addition of water (50 mL) and ether (200 mL) was added to the reaction mixture. The mixture was filtered through celite and the organic phase separated and dried over anhydrous sodium sulfate, filtered, and the solvent removed under vacuum. Chromatography (ethyl acetate-hexanes: 1–4) afforded 8.9 g (96%) of a yellow solid: 31–33° C.

Elemental analysis calculated for $C_6H_4N_3ClO$ Theory: C, 41.52: H, 2.32: N, 8.07 Found: C, 41.16: H, 2.18: N, 8.02

INTERMEDIATE 2

2-Amino-5-chloro-phenol

To a solution of 2-nitro-5-chloro-phenol (2.2 g, 14.0 mmol) in ethanol (40 mL) was added $PtS_2$-C (5%, 200 mg) and hydrogenated at 45 psi for 4 hours. The mixture was filtered through celite and washed with ethyl acetate (100 mL). The solvent was evaporated and purified by chromatography ((ethyl acetate-hexanes: 2–3) to afford 1.89 g (95%) of a light brown solid. Recrystallization afforded an analytical sample: mp 149–151° C.

Elemental analysis calculated for $C_6H_6N_3ClO$ Theory: C, 50.20: H, 4.21: N, 9.78 Found: C, 49.88: H, 4.20: N, 10.06

INTERMEDIATE 3

Ethyl 7-chloro-2,3-dihydro-benzo[1,4]oxazine-2-carboxylate ester

To a solution of 2-amino-5-chloro-phenol ((1.89 g, 13.2 mmol) in acetone (40 mL) was added potassium carbonate (0.6 g, 4.4 mmol) followed by ethyl 1,2-dibromo-propionic ester (1.14 g, 24.4 mmol) at reflux temperature. After 20 minutes another 0.6 g of potassium carbonate, and 0.64 mL of by ethyl 1,2-dibromo-propionic ester were added, followed by a similar addition of reagents after another 1 hour. The reaction was heated to reflux for 18 hours and the precipitates filtered off and the solvent removed under vacuum. The residue was dissolved in cold 1N sodium hydroxide (100 mL) and extracted with ether (3×100mL). The combined organic layers were washed with water (100 mL) and dried over anhydrous sodium sulfate, filtered, and the solvent removed under vacuum. Chromatography (ethyl acetate hexanes: 1–2) afforded 2.3 g (72%) of a red solid: mp 82–84° C.

Elemental analysis calculated for $C_{11}H_{12}NClO_3$ Theory: C, 54.67: H, 5.00: N, 5.79 Found: C, 54.27: H, 4.82: N, 5.71

INTERMEDIATE 4

(4-Methoxy-2-nitro-phenoxy)-malonic acid diethyl ester

A mixture of 5-methoxy-2-nitro phenol ( 2.0 g, 12.2 mmol), diethyl bromo malonate (3.5 g, 14.7 mmol), and potassium carbonate (3.4 g, 24.5 mmol) in 2-butanone (70 mL) was heated to reflux for 18 hours. The inorganic salts were filtered and the solvent removed under vacuum. Chromatography (ethyl acetate-hexanes, 1—1) afforded 3.5 g (87%) of product as a yellow oil: MS (EI) m/e 327 (M+).

INTERMEDIATE 5

7-Methoxy-3-oxo-3,4-dihydro-2H-benzo[1,4] oxazine-2-carboxylic acid ethyl ester

A mixture of (4-methoxy-2-nitro-phenoxy)-malonic acid diethyl ester (2.3 g, 7.0 mmol) in ethanol containing 10% Pd/C was hydrogenated at 35 psi for 18 hours. The catalyst was filtered through celite and the solvents were removed under vacuum to afford a solid which was washed with ether to afford 1.25 g of a white solid. The mother liquor was concentrated and the solid again washed with ether to afford another 100 mg of product. Yield: (1.35 g, 76%): mp 138.5–139.5° C.

Elemental analysis calculated for $C_{12}H_{13}NO_5$ Theory: C, 57.37: H, 5.22: N, 5.58 Found: C, 57.36: H, 5.08: N, 5.80

INTERMEDIATE 6

(3,4-Dihydro-2H-benzo[1,4]oxazin-2-yl)-methanol

To a solution of ethyl 2,3-dihydro-benzo[1,4]oxazine-2-carboxylate ester (11.9 g, 19.0 mmol) in anhydrous tetrahydrofuran (60 mL) was added a 2 M solution of lithium borohydride (15 mL) at room temperature. The reaction was stirred for 1 hour and then quenched by the slow addition of methanol. After 2 hours water was slowly added (100 mL) and the reaction mixture was extracted with ethyl acetate (4×100 mL). The organic layer was separated and dried over anhydrous magnesium sulfate, filtered, and the solvent removed under vacuum. Purification by chromatography (ethyl acetate-hexane-methanol-3:6:1) to afford 1.96 g (62%) of an oil: MS (EI) m/e 165 (M+).

6b) (7-Methoxy-3,4-dihydro-2H-benzo[1,4]oxazin-2-yl)-methanol was prepared in a similar fashion using 7-methoxy-3-oxo-3,4-dihydro-2H-benzo[1,4]oxazine-2-carboxylic acid ethyl ester (2.0 g, 8.0 mmol) in 49% yield (760 mg) as a brown oil: MS (EI) m/e 196 (M+).

INTERMEDIATE 7

2-Hydroxymethyl-2,3-dihydro-benzo[1,4]oxazine-4-carboxylic acid tert-butyl ester To a solution of (3,4 -dihydro-2H-benzo[1,4]oxazin-2-yl)-methanol (10.7 g, 65.0 mmol) prepared above in anhydrous tetrahydrofuran (200 mL) was slowly added di-tert-butyl dicarbonate (62 g) in tetrahydrofuran (40 mL). The reaction was heated to reflux for 4 hours and allowed to cool to room temperature and then poured into water (100 mL) and extracted with ethyl ether (3×100 mL). The organic layer was washed with water (2×50 mL) and the organic layer dried over anhydrous sodium sulfate, filtered, and the solvent removed under vacuum. Chromatography (ethyl acetate-hexanes: 1:2) afforded 12.9 g of white solid (75%): mp 93.5–94.5° C.; MS (EI) m/e 265 (M+).

Elemental analysis calculated for $C_{14}H_{19}NO_4$ Theory: C, 63.38: H, 7.22: N, 5.28 Found: C, 63.53: H, 7.32: N, 5.38

7b) 2-Hydroxymethyl-7-methoxy-2,3-dihydro-benzo[1,4]oxazine-4-carboxylic acid tert-butyl ester was prepared from (7-methoxy-3,4-dihydro-2H-benzo[1,4]oxazin-2-yl)-methanol (1.75 g, 7.0 mmol) as described above in 86% yield (470 mg) as a clear oil: MS (EI) m/e 295 (M+).

INTERMEDIATE 8

2-(Toluene-4-sulfonyloxymethyl)-2,3-dihydro-benzo [1,4]oxazine-4-carboxylic acid tert-butyl ester To a solution of 2-hydroxymethyl-2,3-dihydro-benzo[1,4]oxazine-4-carboxylic acid tert-butyl ester (2.8 g, 10.6 mmol) and p-toluenesulfonyl chloride (3.4 g, ) in anhydrous pyridine (45 mL) was allowed to stir overnight at room temperature. The reaction mixture was quenched with 1 N sodium hydroxide (50 mL) and extracted with methylene chloride (5×50 mL). The organic layer was washed with water (3×50 mL) and the organic layer dried over anhydrous sodium sulfate, filtered and the solvent removed under vacuum. Chromatography (ethyl acetate-hexane, 1–3) afforded a thick oil: MS (FAB) m/e 419 (M+Na).

Elemental analysis calculated for $C_{21}H_{25}NO_6S$ Theory: C, 60.13: H, 6.01: N, 3.34 Found: C, 60.13: H, 6.11: N, 3.56

8b) 2-(Toluene-4-sulfonyloxymethyl)-7-methoxy-2,3-dihydro-benzo[1,4]oxazine-4-carboxylic acid tert-butyl ester (1.4 g, 3.1 mmol) was prepared from 2-hydroxymethyl-7-methoxy-2,3-dihydro-benzo[1,4]oxazine-4-carboxylic acid tert-butyl ester (1.1 g, 3.7 mmol) as described above in 83% yield as a thick yellow oil: MS (EI) m/e 449 (M+).

INTERMEDIATE 9 t-Butyl-2,3-dihydro-benzo[1,4]oxazine-4-carboxylate-2-methylazide

A solution of t-butyl-2,3-dihydro-benzo[1,4]oxazine-4-carboxylate-2-methyltosylate (14.2 g, 33.9 mmol) and sodium azide (4.4 g, 67.7 mmol) in anhydrous dimethylformamide (150 mL) was heated to 60° C. for 20 hours. The reaction mixture was poured into water (150 mL) and extracted with methylene chloride (3×150 mL). The combined organic layers were dried over anhydrous sodium sulfate, filtered and the solvent removed under vacuum. Purification by chromatography (hexanes) afforded 8.7 g (88%) of a white solid: mp 82–83° C.

Elemental analysis calculated for $C_{14}H_{18}N_4O_3$ Theory: C, 57.92: H, 6.25: N, 19.30 Found: C, 58.07: H, 6.21: N, 19.03

INTERMEDIATE 10 t-Butyl-2,3-dihydro-benzo[1,4]oxazine-4-carboxylate-2-methylamine

To a solution of t-butyl-2,3-dihydro-benzo[1,4]oxazine-4carboxylate-2-methylazide (6.25 g, 21.6 mmol) and triphenylphosphine (6.4 g) in tetrahydrofuran (150 mL) containing water (4 mL) was allowed to stir at room temperature for 18 hours. The solvent was removed under vacuum. The residue was dissolved in ethyl ether (100 mL), followed by the addition of hexanes (50 mL). The precipitated triphenylphosphine oxide was filtered off and the solvent removed. Purification by chromatography (5% methanol-methylene chloride) afforded 7.2 g of product (which contained a small amount of triphenylphosphine oxide).: MS (FAB) m/e 265 (M+H)$^+$.

INTERMEDIATE 11

N-(3,4-dihydro-2H-benzo[1,4]oxazin-2-ylmethyl)-3-(1H-indol-3-yl)-propionamide-4-carboxylic acid tert-butyl ester A solution of 3-dimethylamino-propyl-3-ethyl carbodiimide hydrochloride (4.4 g, 22.8 mmol) and 3-indole propionic acid (4.3 g, 22.7 mmol) in methylene chloride (100 mL) was stirred at room temperature. After 0.5 hours a solution of t-butyl-2,3-dihydro-benzo[1,4]oxazine4-carboxylate-2-methylamine (3.0 g, 11.4 mmol) in methylene chloride (5 mL) was added and allowed to stir for 18 hours. The reaction mixture was poured into water (50 mL) and extracted with methylene chloride (3×100 mL). The organic layer was washed with water (2×100 mL), followed by 1 N wsodium hydroxide (2×50 mL) and dried over anhydrous sodium sulfate, filtered, and the solvent removed under vacuum. Initial chromatography using 5 % methanol-methylene chloride allowed removal of the triphenylphosphine oxide. Another chromatography (methylene chloride-acetone: 4;1) afforded 3.7 g (61%) of product as a white foam: MS (FAB) m/z 436 (M+H)$^+$ Elemental analysis calculated for $C_{25}H_{29}N_3O_3$ Theory: C, 68.95: H, 6.71: N, 9.65 Found: C, 68.12: H, 6.72: N, 9.28

INTERMEDIATE 12

N-(3,4-Dihydro-2H-benzo[1,4]oxazin-2-ylmethyl)-3-(1H-indol-3-yl)-propionamide

To a solution of N-(3,4-dihydro-2H-benzo[1,4]oxazin-2-ylmethyl)-3-(1H-indol-3-yl)-propionamide-4-carboxylic acid tert-butyl ester (2.2 g, 5.1 mmol) in methylene chloride (100 mL) was added trifluoroacetic acid (20 mL) in methylene chloride (20 mL). The reaction mixture was stirred at room temperature for 2 hours. The reaction mixture was poured into saturated aqueous sodium sulfate (100 mL) and extracted with methylene chloride (2×30 mL). The organic layer was again washed with saturated sodium sulfate, followed by water (100 mL). The organic layer was dried over anhydrous magnesium sulfate, filtered, and the solvent removed under vacuum. Purification by chromatography (5% methanol-methylene chloride) afforded 1.4 g (83%) of product as a white solid: mp 145–146° C.; MS (FAB) m/z 336 (M+H)$^+$

INTERMEDIATE 13

{[3-(5-Fluoro-1H-indol-3-yl)-propylaniinol]-methyl}-3,4-dihydro-benzo[1,4]oxazine4-carboxylic acid tert-butyl ester A solution of t-butyl-2,3-dihydro-benzo[1,4]oxazine-4-carboxylate-2-methylamine (0.9 g, 3.4 mmol), 5-fluoro-indolyl-3-propylbromide [0.58 g, 2.3 mmol; prepared from 3-(5-fluoro-1H-indol-3-yl)-propan-1-ol, in the manner described in *J. Med. Chem.* 1976, 19, 391–395. using CBr$_4$ and triphenylphosphine], triethylamine (0.345 g, 3.4 mmol) in dimethylsulfoxide (20 mL) was heated to 90° C. for 12 hours. The reaction was quenched with water (100 mL) and extracted with methylene chloride (3×100mL). The combined organic layers were dried over anhydrous sodium sulfate, filtered, and the solvent removed under vacuum. Chromatography (5% methanol-methylene chloride) afforded 0.49 g (49%) of a yellow oil: MS (EI) m/e 439 (M$^+$).

13b) {[3-(5-Fluoro-1H-indol-3-yl)-propylamino]-methyl}-7-methoxy-3,4dihydro-benzo[1,4]oxazine-4carboxylic acid tert-butyl ester (300 mg, 0.64 mmol) was prepared under the condition described above by using t-butyl-7-methoxy-2,3-dihydro-benzo[1,4]oxazine-4-carboxylate-2-methyltosylate (416 mg, 0.92 mmol) and treating with 5-fluoro-indolyl -3-propylamine (0.356 g, 1.85 mmol) in 70% yield as a yellow glass: MS (EI) m/e 469 (M+).

INTERMEDIATE 14 (Method a)

(4-Benzyl-3,4-dihydro-2H-benzo[1,4]oxazin-2-yl)-methanol

To a solution of (3,4-dihydro-2H-benzo[1,4]oxazin-2-yl)-methanol (4.0 g, 24.0 mmol) in anhydrous acetonitrile (60 mL) was added benzyl bromide (8.6 mL) and stirred at room temperature for 2 hours. The reaction was quenched with water (50 mL) and extracted with methylene chloride (3×100 mL). The combined organic layers were dried over anhydrous sodium sulfate, filtered, and the solvent evaporated under vacuum. Chromatography (2.5% methanol-methylene chloride) afforded 3.7 g (60%) of product as a yellow oil: MS (FAB) m/e 255 (M+).

14b) Ethyl 4-propyl-2,3-dihydro-benzo[1,4]oxazine-2-carboxylate ester was prepared as a yellow oil in 28% yield by reacting ethyl 2,3-dihydro-benzo[1,4]oxazine-2-carboxylate ester ( 3.6 g, 17 mmol) and 1-iodopropane (8.6 g, 5.0 mmol) as described above.

Elemental analysis calculated for $C_{14}H_{19}NO_3$ Theory: C, 67.45: H, 7.68: N, 5.62 Found: C, 67.79: H, 7.71: N, 5.51

14c) Ethyl 7-chloro-4methyl-2,3-dihydro-benzo[1,4]oxazine-2-carboxylate ester was prepared by treatment of ethyl 7-chloro-2,3-dihydro-benzo[1,4]oxazine-2-carboxylate ester (2.2g, 9.2 mmol) with methyl iodide (3.9 g, 28 mmol) according to the above procedure in 50% yield (1.18 g) as a brown oil: MS (EI) m/e 255 (M+).

14d) (4-Isopropyl-3,4-dihydro-2H-benzo[1,4]oxazin-2-yl)-methanol In a similar fashion the title compound was prepared by replacing benzyl bromide with isopropyl bromide in 28% yield (1.6 g) as a yellow oil: MS (EI) m/e 207 (M$^+$).

Elemental analysis calculated for $C_{12}H_{17}NO_2$ Theory: C, 69.80: H, 8.27: N, 6.76 Found: C, 69.10: H, 8.13: N, 6.80

INTERMEDIATE 14e (Method b)

4-Isobutyryl-3,4-dihydro-2H-benzo[1,4]oxazine-2-carboxylic acid ethyl ester

To a solution of ethyl 2,3-dihydro-benzo[1,4]oxazine-2-carboxylate ester (3.0 g, 14.5 mmol), isobutyric acid anhydride (11.4 g, 72 mmol) in tetrahydrofuran (40 mL) was heated to reflux for 18 hours. The reaction was poured into aqueous saturated sodium bicarbonate (50 mL) and extracted with methylene chloride (3×100 mL). The organic layer was dried over anhydrous sodium sulfate, filtered, and the solvent removed under vacuum. Chromatography (ethyl acetate-hexanes: 1–4) afforded 3.4 g (85%) of product as a yellow oil: MS (EI) m/e 277 (M+).

Elemental analysis calculated for $C_{15}H_{1719}NO_4$ Theory: C, 64.97: H, 6.91: N, 5.05 Found: C, 64.32: H, 7.00: N, 4.81

14f) 4-Acetyl-3,4-dihydro-2H-benzo[1,4]oxazine-2-carboxylic acid ethyl ester was prepared in 48% yield as a yellow oil by reacting ethyl 2,3-dihydro-benzo[1,4]oxazine-2-carboxylate ester (3.5 g, 17 mmol) and acetic anhydride (11.3 g, 85 mmol) as described above in method b: MS (EI) m/e 249 (M+).

INTERMEDIATE 15

(4-Isobutyl-3,4-dihydro-2H-benzo[1,4]oxazin-2-yl)-methanol

To a solution of 4-isobutyryl-3,4dihydro-2H-benzo[1,4]oxazine-2-carboxylic acid ethyl ester (3.4 g, 12 mmol) in anhydrous tetrahydrofuran (50 mL) at room temperature was added lithium aluminum hydride (61 mL of 1M solution in tetrahydrofuran, 61 mmol). The reaction was allowed to heat at reflux for 18 hours and the reaction was cautiously quenched by sequentially adding water (4 mL), 15% NaOH (4 mL), and water (12 mL). The precipitate was filtered and washed with ethyl acetate. The solvent was evaporated under vacuum and the product chromatographed (ethyl acetate-hexanes; 2:3) to afford 1.1 g (25%) of product as a yellow oil: MS (EI) m/e 221 (M+).

15b) (4-Ethyl-3,4-dihydro-2H-benzo[1,4]oxazin-2-yl)-methanol was prepared as a yellow oil in 67% yield by reacting intermediate 4-acetyl-3,4-dibydro-2H-benzo[1,4]oxazine-2-carboxylic acid ethyl ester as described above: MS (EI) m/e 193 (M+).

15c) (4-Propyl-3,4-dihydro-2H-benzo[1,4]oxazin-2-yl)-methanol was prepared as a yellow oil as described above in 78% yield (0.75 g) by using ethyl 4-propyl-2,3-dihydro-benzo[1,4]oxazine-2-carboxylate ester (1.15 g, 4.6 mmol).

Elemental analysis calculated for $C_{12}H_{17}NO_2$ Theory: C, 69.54: H, 8.27: N, 6.76 Found: C, 69.21: H, 8.07: N, 6.81

15d) (7-Chloro-4-methyl-3,4-dihydro-2H-benzo[1,4]oxazin-2-yl)-methanol was prepared as a yellow oil as described above in 98% yield (0.91 g) by using ethyl 7-chloro-4-methyl-2,3-dihydro-benzo[1,4]oxazine-2-carboxylate ester (1.1 g, 4.3 mmol): MS (EI) m/e 213 (M+)

INTERMEDIATE 16

Toluene sulfonic acid 4-benzyl-3,4-dihydro-2H-benzo[1,4]oxazin-2-yl-methy ester

A solution of (4-benzyl-3,4-dihydro-2H-benzo[1,4]oxazin-2-yl)-methanol (3.9 g, 15.4 mmol) and tosyl chloride (4.2 g) in anhydrous pyridine (80 mL) was stirred for 18 hours and then poured into 1 N HCl (200 mL). The mixture was extracted with methylene chloride (3×100 mL) and the combined organic layers were washed with 1 N HCl (50 mL), followed by brine (100 mL), then dried over anhydrous sodium sulfate, filtered, and the solvent removed under vacuum. Chromatography (ethyl acetate-hexanes: 1:4) afforded 6.2 g (98%) of a light yellow oil: MS (FAB) m/z 409 (M+H)+

16b) Toluene sulfonic acid 4-isopropyl-3,4dihydro-2H-benzo[1,4]oxazin-2-ylmethy ester was prepared in a similar fashion using (4-isopropyl-3,4-dihydro-2H-benzo[1,4]oxazin-2-yl)-methanol in 89% yield as a yellow oil: MS (EI) m/e 361 (M+).

Elemental analysis calculated for $C_{19}H_{23}NO_4S$ Theory: C, 63.14: H, 6.41: N, 3.80 Found: C, 62.33: H, 6.22: N, 3.70

16c) Toluene sulfonic acid 4-isobutyl-3,4-dihydro-2H-benzo[1,4]oxazin-2-ylmethyl ester was prepared as above using (4-isobutyl-3,4-dihydro-2H-benzo[1,4]oxazin-2-yl)-methanol in 59% yield as a yellow oil.

Elemental analysis calculated for $C_{20}H_{25}NO_4S$ Theory: C, 63.98: H, 6.71: N, 3.73 Found: C, 63.71: H, 6.58: N, 3.55

INTERMEDIATE 17

(4-Benzyl-3,4-dihydro-2H-benzo[1,4]oxazin-2-yi)-methylazide

A solution of toluene sulfonic acid 4-benzyl-3,4-dihydro-2H-benzo[1,4]oxazin-2-yl-methyl ester (7.2 g, 17.6 mmol) and sodium azide (2.3 g, 34 mmol) in anhydrous dimethylformamide (40 mL) was heated to 60° C. for 1 day. The mixture was poured into water (200 mL) and extracted with methylene chloride (3×100mL). The combined organic layers were washed with water (50 mL) and dried over anhydrous sodium sulfate, filtered, and the solvent removed under vacuum. Chromatography (ethyl acetate-hexanes: 1–5) provided 3.6 g (72%) of a yellow oil.

Elemental analysis calculated for $C_{16}H_{16}N_4O_1$ Theory: C, 68.55: H, 5.75: N, 19.99 Found: C, 68.38: H, 5.56: N, 19.85

INTERMEDIATE 18

(4-Benzyl-3,4-dihydro-2H-benzo[1,4]oxazin-2-yl)-methylamine (4-Benzyl-3,4-dihydro-2H-benzo[1,4]oxazin-2-yl)-methylazide (3.5 g, 12 mmol) was reacted according to the procedure used for Intermediate 10 to afford 2.3 g (73%) of the title compound as a yellow oil. The oxalate salt was prepared in ethanol: mp 214–215° C.

Elemental analysis calculated for $C_{16}H_{18}N_2O$ Theory: C, 62.72: H, 5.85: N, 8.13 Found: C, 62.58: H, 5.76: N, 8.04

INTERMEDIATE 18b (Method b)

(4-Methyl-3,4-dihydro-2H-benzo[1,4]oxazin-2-yi)-methylamine

To a solution of t-butyl-2,3-dihydro-benzo[1,4]oxazine-4-carboxylate-2-methylazide (1.9 g, 6.5 mmol) in anhydrous tetrahydrofuran (30 mL) was added 32 mL of 1M lithium aluminum hydride in tetrahydrofuran and heated to reflux for 18 hours. The reaction mixture was quenched with a saturated solution of ammonium chloride and the precipitate filtered through celite. The celite was washed with methanol containing 1% aqueous ammonium hydroxide. The solvent was evaporated under vacuum and the product purified by chromatography (10% methanol-methylene chloride) to afford 0.45 g of the title compound as a yellow oil: MS (FAB) m/z 179 (M+H)+.

INTERMEDIATE 19

N-(4-Benzyl-3,4-dihydro-2H-benzo[1,4]oxazin-2-ylylmethyl)-3-(1H-indol-3-yl)-propionamide (4-Benzyl-3,4-dihydro-2H-benzo[1,4]oxazin-2-yl)-methylamine (0.9 g, 3.5 mmol) was coupled to indole propionic acid (1.6 g, 8.2 mmol) according to the procedure used to prepare intermediate 11 above to afford 1.5 g (98%) of the title compound as a white solid: mp 39–61° C.; MS (EI) m/e 425 (M+).

Elemental analysis calculated for $C_{27}H_{27}N_3O_2$ Theory: C, 76.21: H, 6.39: N, 9.87 Found: C, 75.40: H, 6.53: N, 9.46

19b) N-(4-Benzyl-3,4-dihydro-2H-benzo[1,4]oxazin-2-ylylmethyl)-3-(1H-indol-3-yl)-butyramide. (4-Benzyl-3,4-dihydro-2H-benzo[1,4]oxazin-2-yl)-methylamnine (1.2 g, 4.7 mmol) was coupled to indole butyric acid (1.8 g, 8.9 mmol) according to the procedure used to prepare intermediate1 1 above to afford 1.3 g (63%) of the title compound as a yellow solid: mp 61–63.5° C.; MS (EI) m/e 439 ($M^+$)

INTERMEDIATE 20

Ethyl 4-phenyl-2,3-dihydro-benzo[1,4]oxazine-2-carboxylate ester

A solution of ethyl 2,3-dihydro-benzo[1,4]oxazine-2-carboxylate ester (10g, 48 mmol), 1,4-cyclohexanedione (10.8 g, 97 mmol) and p-toluenesulfonic acid (2 g) in toluene (200 mL) was heated to reflux for 4 hours. The solvent was evaporated and the product was purified by chromatography (ethyl acetate-hexane: 1–3) to afford 7.2 g (53%) of product as a yellow oil: MS (EI) m/e 283 ($M^+$).

INTERMEDIATE 21

(4-Phenyl-3,4-dihydro-2H-benzo[1,4]oxazin-2-yl)-methanol

To a solution of ethyl 4-phenyl-2,3-dihydro-benzo[1,4] oxazine-2-carboxylate ester (6.9 g, 24 mmol) in anhydrous tetrahydrofuran (80 mL) was added 60 mL of 2 M lithium borohydride in tetrahydrofuran (0.12 mol) at room temperature. The reaction mixture was stirred at room temperture for 4 hours and quenched with methanol. The reaction was poured into water (100 mL) and extracted with ether (3×80 mL) and the combined organic layers dried over anhydrous sodium sulfate, filtered, and the solvent removed under vacuum. Chromatography (ethyl aceate-hexanes; 1–3) afforded 5.7 g (96%) of product as a clear oil: MS (EI) m/e 213 ($M^+$).

Elemental analysis calculated for $C_{15}H_{15}NO_2$ Theory: C, 74.67: H, 6.27: N, 5.81 Found: C, 74.21: H, 6.60: N, 5.56

INTERMEDIATE 22

Toluene sulfonic acid 4phenyl-3,4-dihydro-2H-benzo[1,4]oxazin-2-yl-methyl ester (4-Phenyl-3,4-dihydro-2H-benzo[1,4]oxazin-2-yl)-methanol (5.6 g, 23 mmol) was reacted according to the procedure as described above for Intermediate 8 to afford 8.2 g (89%) of the title compound: mp 83–85° C.

Elemental analysis calculated for $C_{21}H_{21}NO_4S$ Theory: C, 66.82: H, 5.35: N, 3.80 Found: C, 66.53: H, 5.39: N, 3.40

22b) Toluene-4-sulfonic acid 4-ethyl-3,4-dihydro-2H-benzo[1,4]oxazin-2-yl-methyl ester was prepared as described above using (4-ethyl-3,4-dihydro-2H-benzo[1,4] oxazin-2-yl)-methanol in 32% yield as a bluish solid: mp 85–87° C: MS (EI) m/e 347 ($M^+$).

22c) Toluene-4-sulfonic acid 4-propyl-3,4-dihydro-2H-benzo[1,4]oxazin-2-yl-methyl ester was prepared as described above as a thick oil in 83% yield by using (4-propyl-3,4-dihydro-2H-benzo[1,4]oxazin-2-yl)-methanol: MS EI m/e 361 ($M^+$).

22d) Toluene-4sulfonic acid 7-chloro-4-methyl-3,4-dihydro-2H-benzo[1,4]oxazin-2-yl-methyl ester was prepared as described above as a blue solid in 87% yield by using (7-chloro-4-methyl-3,4-dihydro-2H-benzo[1,4] oxazin-2-yl)-methanol: mp 65–67° C.; MS EI m/e 367 ($M^+$).

INTERMEDIATE 24

5-Fluoro-3-(3-p-toluenesulfonyloxypropyl)indole

To a stirred solution of 3-(5-fluoro-1H-indol-3-yl)-propan-1-ol (2.90 g, 15.0 mmol) in pyridine (15.0 mL) was added p-toluenesulfonyl chloride (7.1 g, 37.5 mmol) at room temperature. After stirring for 30 minutes at room temperature, the reaction mixture was poured to 200 mL of ice water. The aqueous was extracted with ethyl acetate and the combined organic extracts were washed with 1N HCl, brine, dried over anhydrous sodium sulfate, filtered, and the solvent was concentrated. The crude product was purified by silica gel column chromatography (ethyl acetate/hexane, 3/7) to give 4.1 g (79%) of the title compound as a solid: mp 74° C. (Lit. mp 99° C.; EP 464604 A2).

The following non-limiting examples illustrate the preparation of representative compounds of this invention.

EXAMPLE 1

(3,4)-Dihydro-2H-benzo[1,4]oxazin-2-yl-methyl)-[3-(1H-indo-3-yl)-propyl]-amine

To a solution of lithium aluminum hydride (0.78 g), in anhydrous tetrahydrofuran (20 mL) was added 1.1 g of N-(3,dihydro-2H-benzo[1,4]oxazin-2-ylylmethyl)-3-(1H-indol-3-yl)-propionamide in tetrahydrofuran (20 mL). The reaction mixture was allowed to reflux for 18 hours then cooled to room temperature and quenched with aqueous ammonium chloride. The precipitate was filtered through celite and the solvent removed under vacuum. Purification by chromatography (5% methanol:methylene chloride) provided 0.9 g (90%) of a white foam: MS (EI) m/e 321 ($M^+$).

The fumarate salt was prepared in ethanol: mp 203–204° C.

Elemental analysis calculated for $C_{20}H_{23}N_3O_3 \cdot C_4H_4O_4$ Theory: C, 68.55; H, 6.01; N, 10.90 Found: C, 68.93; H, 6.47; N, 10.98

EXAMPLE 2

3-(1H-Indol-3-yl)-propyl]-(4-methyl-3,4-dihydro-2H-benzo[1,4]oxazin-2-yl-methyl)-amine To a solution of lithium aluminum hydride (0.69 g) in anhydrous tetrahydrofuran (50 mL) was added {[3-(1H-indol-3-yl)-1-oxo-propylamino]-methyl}-3,4-dihydro-benzo[1,4]oxazine-4-carboxylic acid tert-butyl ester (1.3 g, 3.0 mmol) in tetrahydrofuran (10 mL) at 0° C. The reaction mixture was heated to reflux for 18 hours and then quenched with aqueous ammonium chloride and the solids filtered through celite. The solvent was removed under vacuum and the product was purified by chromatography (5% methanol-methylene) to provide 0.51 g (51%) as a pale-yellow solid: mp 110–112° C. The fumarate salt was prepared in ethanol to afford yellow crystals: mp 196.5–197.5° C.

Elemental analysis calculated for $C_{21}H_{23}N_3O_3 \cdot C_4H_4O_4$ Theory: C, 66.5; H, 6.47; N, 9.31 Found: C, 66.21; H, 6.38; N, 9.18

EXAMPLE 3

(4-Benzyl-3,4-dihydro-2H-benzo[1,4]oxazin-2ylmethyl)-[3-(1H-indo-3-yl)-propyl]-amine This compound was prepared from N-(4-benzyl-3,4-dihydro-2H-benzo[1,4]oxazin-2-ylmethyl)-3-(1H-indol-3-yl)-propionamide according to the procedure set forth in Example 2 to provide an 87% yield. The fumarate salt was prepared in isopropanol: mp 174–176° C.

Elemental analysis calculated for $C_{27}H_{29}N_3O \cdot C_4H_4O_4$ Theory: C, 70.57; H, 6.3; N, 7.96 Found: C, 70.26; H, 6.23; N, 7.8

EXAMPLE 4

(4-Benzyl-3,4-dihydro-2H-benzo[1,4]oxazin-2ylmethyl)-[3-(1H-indo-3-yl)-butyl]-amine This compound was prepared from N-(4-benzyl-3,4-dihydro-2H-benzo[1,4]oxazin-2-ylmethyl)-3-(1H-indol-3-yl)-butyramide according to the procedure set forth in Example 2 to provide a 73% yield. The fumarate salt was prepared in ethanol: mp 171.5–172.5° C.

Elemental analysis calculated for $C_{28}H_{31}N_3O \cdot 0.5 C_4H_4O_4$ Theory: C, 74.51; H, 6.88; N, 8.69 Found: C, 74.12; H, 6.80; N, 8.61

EXAMPLE 5

[3-(5-Fluoro-1H-indol-3-yl)-propyl]-(4-methyl-3,4-dihydro-2H-benzo[1,4]oxazin-2-yl-methyl)-amine A solution of 4-methyl-3,4-dihydro-2H-benzo[1,4]oxazin-2-yl-methylamine (0.45 g, 2.5 mmol) and 5-fluoro-indolyl-3-propylbromide (0.6 g, 2.5 mmol), and triethylamine (0.5 g) in dimethylsulfoxide (20 mL) was heated to 100° C. for 10 hours. The reaction mixture was poured into water (100 mL) and extracted with methylene chloride (3×50 mL). The combined organic layers were dried over anhydrous sodium sulfate, filtered, and the solvent removed under vacuum. Chromatography (10% methanol-methylene chloride) afforded 0.42 g (47%) of desired product as a yellowish brown oil. The oxalate salt was prepared in ethanol: mp 189–190° C.

Elemental analysis calculated for $C_{21}H_{21}N_3O \cdot C_2H_2O_4$ Theory: C, 62.25; H, 5.91; N, 9.47 Found: C, 62.03; H, 6.06; N, 9.41

EXAMPLE 6

[3-(1H-Indol-3-yl)-propyl]-4-benzyl-3,4-dihydro-2H-benzo[1,4]oxazin-2 yl-methyl)-amine This compound was prepared in 63% yield as a yellow oil as described in Example 5 by reacting 4-benzyl-3,4-dihydro-2H-benzo[1,4]oxazin-2-yl)-methylamine (0.21 g, 0.83 mmol) with 3-(5-fluoro-3-indolylpropylamine (0.14 g, 5.5 mmol) to provide a 63% yield. The oxalate salt was prepared in ethanol: mp 212–214° C.

Elemental analysis calculated for $C_{27}H_{28}N_3OF \cdot C_2H_2O_4$ Theory: C, 66.46; H, 5.87; N, 8.02 Found: C, 66.29; H, 5.74; N, 8.04

EXAMPLE 7

[3-(1H-Indol-3-yl)-propyl]-4-phenyl-3,(4-dihydro-2H-benzo[1,4]oxazin-2-yl-methyl)-amine A mixture of toluene sulfonic acid 4-phenyl-3,4-dihydro-2H-benzo[1,4]oxazin-2-yl-methyl ester (1.2 g, 3.0 mmol) and 3-(3-indolyl)propylamine (1.13 g, 6 mmol) in dimethylsulfoxide (20 mL) was heated to 100° C. for 12 hours. The reaction mixture was poured into water (100 mL) and extracted with methylene chloride (3×100 mL). The combined orgainic layers were washed with water (3×100 mL) and dried over anhydrous sodium sulfate, filtered, and the solvent removed under vacuum. Chromatography (5% methanol-methylene chloride) afforded 0.96 g (80%) of product as a yellow oil. The fumarate salt was prepared in ethanol: mp 197–198° C.

Elemental analysis calculated for $C_{26}H_{27}N_3O \cdot C_4H_4O_4$ Theory: C, 69.55; H, 6.13; N, 8.11 Found: C, 69.61; H, 5.98; N, 8.04

EXAMPLE 8

[3-(5-Fluoro-1H-indol-3-yl)-propyl]-(4-isopropyl-3,4-dihydro-2H-benzo[1,4]oxazin-2yl-methyl)-amine This compound was prepared in a 40% yield in the manner described in Example 7 by reacting toluene sulfonic acid 4isopropyl-3,4dihydro-2H-benzo[1,4]oxazin-2-yl-methyl ester (1 g, 2.8 mmol) with 3-(5-fluoro-3-indolyl) propylamine (0.8 g, 4.2 mmol). The oxalate salt was prepared in ethanol: mp 204–206° C.

Elemental analysis calculated for $C_{23}H_{28}N_3OF \cdot C_2H_2O_4$ Theory: C, 63.64; H, 6.41; N, 8.91 Found: C, 63.31; H, 6.47; N, 9.1

EXAMPLE 9

[3-(1H-indol-3-yl)-butyl]-4-isopropyl-3,(4-dihydro-2H-benzo [1,4]oxazin-2-yl-methyl)-amine This compound was prepared in a 52% yield as a yellow oil in the manner described in Example 7 by reacting toluene sulfonic acid 4-isopropyl-3,4-dihydro-2H-benzo[1,4]oxazin-2-yl-methyl ester(0.75 g, 2.1 mmol) with 3-(3-indolyl)butylamine (0.51 g, 2.7 mmol). The oxalate salt was prepared in ethanol: mp 166.5–168° C.

Elemental analysis calculated for $C_{24}H_{31}N_3O \cdot C_2H_2O_4$ Theory: C, 66.74; H, 7.11; N, 8.98 Found: C, 66.45; H, 6.91; N, 8.88

EXAMPLE 10

[3-(5-Fluoro-1H-indol-3-yl)-propyl]-4-isobutyl-3,4-dihydro-2H-benzo[1,4]oxazin-2-yl-methyl)-amine This compound was prepared as a yellow solid in a 56% yield in the manner described in Example 7 by reacting toluene sulfonic acid 4-isobutyl-3,4-dihydro-2H-benzo[1,4]oxazin-2-yl-methyl ester (0.69 g, 1.8 mmol) with 3-(5-fluoro-3-indolyl)propylamine (0.53 g, 2.8 mmol): mp 99–101.5° C. The oxalate salt was prepared in ethanol: mp 214–215° C.

Elemental analysis calculated for $C_{24}H_{30}N_3OF \cdot C_2H_2O_{4 \cdot 0.5}H_2O$ Theory: C, 63.14; H, 6.73; N, 8.50 Found: C, 63.09; H, 6.53; N, 8.63

EXAMPLE 11

[3-(5-Fluoro-1H-indol-3-yl)-propyl]-(4-phenyl-3,4-dihydro-2H-benzo[1,4]oxazin-2-yl-methyl)-amine This compound was prepared as a brown solid in 48% yield in the manner described in Example 7 by reacting toluene sulfonic acid (4-phenyl-3,4-dihydro-2H-benzo[1,4]oxazin-2-yl)-methyl ester (0.8 g, 2.0 mmol) with 3-(5-fluoro-3-indolyl)propylamine (0.58 g, 3.0 mmol): mp 67–70° C. The oxalate salt was prepared in ethanol: mp 179–180° C.

Elemental analysis calculated for $C_{26}H_{26}N_3OF \cdot C_2H_2O_4 \cdot 0.25H_2O$ Theory: C, 65.93; H, 5.63; N, 8.24 Pound: C, 66.00; H, 5.47; N, 8.17

EXAMPLE 12

[3-(5-Fluoro-1H-indol-3-yl)-butyl]-(4-phenyl-3,4-dihydro-2H-benzo[1,4]oxazin-2-yl-methyl)-amine This compound was prepared as a brown solid in 84% yield in the manner described in Example 7 by reacting toluene sulfonic acid 4-phenyl-3,4-dihydro-2H-benzo [1,4] oxazin-2-yl-methyl ester (1.0 g, 2.5 mmol) with 3-(3-indolyl)butylamine (0.95 g, 5.1 mmol). The oxalate salt was prepared in ethanol: mp 175–177° C.

Elemental analysis calculated for $C_{27}H_{29}N_3O \cdot C_2H_2O_4$ Theory: C, 69.40; H, 6.23; N, 8.37 Found: C, 69.27; H, 6.19; N, 8.33

EXAMPLE 13

[3-(-Fluoro-1H-indol-3-yl)-propyl]-(4-ethyl-3,4-dihydro-2H-benzo[1,4]oxazin-2-yl-methyl)-amine This compound was prepared as a yellow solid in a 47% yield by treating toluene sulfonic acid 4-ethyl-3,4-dihydro-2H-benzo[1,4]oxazin-2-yl-methyl ester (0.6 g, 1.7 mmol) with 3-(5-fluoro-3-indolyl)propylamine (0.59 g, 2.6 mmol): mp 127–129° C. The oxalate salt was prepared in ethanol: mp 203–204° C.

Elemental analysis calculated for $C_{22}H_{26}N_3OF \cdot C_2H_2O_4$ Theory: C, 62.96; H, 6.16; N, 9.18 Found: C, 62.81; H, 6.09; N, 9.10

EXAMPLE 14

[3-(5-Fluoro-1H-indol-3-yl)-propyl]-(4-propyl-3,4-dihydro-2H-benzo[1,4]oxazin-2-yl-methyl)-amine This compound was prepared in a 50% yield as a yellow oil in the manner described in Example 13 by reacting toluene sulfonic acid 4-propyl-3,4-dihydro-2H-benzo[1,4]oxazin-2-yl)-methyl ester (0.9 g, 2.5 mmol) with 3-(5-fluoro-3-indolyl)propylamine (0.7 g, 3.7 mmol) .

Elemental analysis calculated for $C_{23}H_{28}N_3OF$ Theory: C, 72.41; H, 7.40; N, 11.02 Found: C, 72.20; H, 7.33; N, 11.01

The oxalate salt was prepared in ethanol: mp 215–216° C.

Elemental analysis calculated for $C_{23}H_{28}N_3OF \cdot C_2H_2O_4$ Theory: C, 63.64; H, 6.41; N, 8.91 Found: C, 63.33; H, 6.45; N, 8.88

EXAMPLE 15

(7-Chloro-4-methyl-3,4-dihydro-2H-benzo[1,4] oxazin-2ylmethyl)-[3-(5-fluoro-1H-indol-3-yl)-propyl]-amine This compound was prepared in a 63% yield as a yellow oil in the manner described in Example 13 by reacting toluene sulfonic acid 7-chloro-4-methyl-3,4-dihydro-2H-benzo[1,4]oxazin-2-yl-methyl ester (0.6 g, 1.6 mmol) and with 3-(5-fluoro-3-indolyl)propylamine (0.63 g, 3.3 mmol) . The fumarate salt was prepared in ethanol: mp 185–186.5° C.

Elemental analysis calculated for $C_{21}H_{23}N_3OFCl \cdot C_4H_4O_4$ Theory: C, 58.58; H, 5.40; N, 8.34 Found: C, 59.44; H, 5.38; N, 8.24

EXAMPLE 16

(3,4-Dihydro-2H-benzo[1,4]oxazin-2ylmethyl)-[3-(5-fluoro-1H-indol-3-yl)-propyl]-amine The title compound was prepared in a 19% yield by reacting {[3-(5-fluoro-1H-indol-3-yl)-propylamino]-methyl}-3,4-dihydro-benzo [1,4]oxazine-4-carboxylic acid tert-butyl ester (0.49 g, 1.1 mmol) with trifluoroacetic acid (20 mL) in methylene chloride (20 mL). The reaction mixture was stirred at room temperature for two hours and then poured into saturated sodium carbonate and extracted with methylene chlloride. The organic layer was dried over anhydrous sodium sulfate, filtered and chromatographed (5% MeOH in methylene chloride) afforded 0.06 g (19%) of product as an oil. The oxalate salt was prepared in ethanol: mp 168–170° C.

Elemental analysis calculated for $C_{20}H_{22}N_3OF \cdot 1.5C_2H_2O_4$ Theory: C, 55.49; H, 5.05; N, 8.09 Found: C, 55.46; H, 5.12; N, 8.39

EXAMPLE 17

7-Methoxy-3,4-dihydro-2H-benzo[1,4]oxazin-2ylmethyl)-[3-(5-Fluoro-1H-indol-3-yl)-propyl]-amine The title compound (186 mg, 0.50 mmol) was prepared according to the procedure of Example 16 by using {[3-(5-fluoro-1H-indol-3-yl)-propylamino]-methyl}-7-methoxy-3,4-dihydro-benzo [1,4]oxazine-4-carboxylic acid tert-butyl ester (290 mg, 0.62 mmol) in 82% yield as a clear glass: MS (EI) m/e 369 (M+). The oxalate salt was prepared from ethanol: mp 190–191° C.

Elemental analysis calculated for $C_{21}H_{24}N_3O_2F \cdot 2.0C_2H_2O4 \cdot 0.25H_2O$ Theory: C, 54.20; H, 5.19; N, 7.58 Found: C, 53.96; H, 5.22; N, 7.41

EXAMPLES 18 and 19

Resolution of [3-(5-Fluoro-1H-indol-3-yl)-propyl]-4-phenyl-3,4-dihydro-2H-benzo[1,4]oxazin-2-yl-methyl)-amine Racemic [3-(5-fluoro- 1 H -indol-3-yl)-propy]-4-pheny-3,4-dihydro-2H-benzo[1,4]oxazin-2ylmethyl)-amine was resolved on a chiracel column to afford 160 mg of (−)-[3-(5-fluoro-1H-indol-3-yl)-propyl]-4-phenyl-3,4-dihydro-2H-benzo[1,4]oxazin-2-yl-methyl)-amine as a yellow oil (100% optical purity). The oxalate salt was prepared in ethanol: mp 198–200° C.; $[\alpha]_D$ −16.7 (c=DMSO, 10.04 mg/ml). DMSO, 10.04 mg/ml Elemental analysis calculated for $C_{26}H_{26}N_3OF \cdot C_2H_2O_4$ Theory: C, 66.48; H, 5.58; N, 8.31 Found: C, 66.29; H, 5.57; N, 8.19 followed by (+)-[3-(5-fluoro-1H-indol-3-yl)-propyl]-4-phenyl-3, 4-dihydro-2H-benzo[1,4]oxazin-2-yl-methyl)-amine (140 mg,) as a yellow oil (99% optical purity). The oxalate salt was prepared in ethanol: (WAY 143399); mp 196–197.5° C.; $[\alpha]_D$ 18.3° (c=DMSO, 9.83 mg/ml). DMSO, 9.83 mg/ml Elemental analysis calculated for $C_{26}H_{26}N_3OF \cdot C_2H_2O_4 \cdot 0.25H_2O$ Theory: C, 65.93; H, 5.63; N, 8.24 Found: C, 65.99; H, 5.53; N, 8.17

EXAMPLE 20

(3,4-Dihydro-2H-benzo[1,4]oxazin-3-yl-methyl)-[3-(5-fluoro-1H-indol-3-yl)propyl]-amine To a solution of 5-fluoro-3-(3-p-toluenesulfonyloxypropyl)indole (0.52 g, 1.5 mmol) and 3-aminomethyl-1,4-benzoxazine (0.25 g, 1.5 mmol) [prepared in accordance with the procedure set forth in *Ind. J. Chem.*, 13:462–467 (1975)] in acetonitrile (15 mL) was added triethylamine (0.42 mL, 3.0 mmol) at room temperature. The reaction mixture was allowed to reflux 18 h, cooled and concentrated. The crude product was purified by silica gel column chromatography (ethyl acetate/methanol/ $NH_4OH$, 98/2/0.5) to afford 265 mg (52%) of the free base.

The fumarate salt was prepared in ethanol: mp 185–187° C.: MS (EI) m/e 339 (M+).

Elemental analysis calculated for $C_{20}H_{22}FN_3O \cdot 0.5C_4O_4$ $0.25H_2O$ Theory: C, 65.74; H, 6.14; N, 10.45 Found: C, 65.71; H, 6.16; N, 10.22

The compounds of the present invention have a high affinity for the 5-HT$_{1A}$ receptor and an ability to inhibit 5-HT transport. Therefore, the present compounds are useful in the treatment of CNS disorders amenable to treatment with antidepressant and anxiolytic agents. The activity of the present compounds is demonstrated by the following standard pharmacological test procedure.

The PCR cloning of the human 5-HT$_{1A}$ receptor subtype from a human genomic library has been described previously in Chanda et al., Mol. Pharmacol., 43:516 (1993). A stable Chinese hamster ovary cell line expressing the human 5-HT$_{1A}$ receptor subtype (5H-HT$_{1A}$ .CHO cells) was employed throughout this procedure. Cells were maintained in DMEM supplemented with 10% fetal calf serum, non-essential amino acids and penicillin/streptomycin.

Cells were grown to 95–100% confluency as a monolayer before membranes were harvested for binding studies. Cells were gently scraped from the culture plates, transferred to centrifuge tubes, and washed twice by centrifugation (at 2000 rpm for 10 min., 4° C.) in buffer (50 mM Tris; pH 7.5). The resulting pellets were aliquoted and stored at –80° C. until needed. On the day of assay, the cells were thawed on ice, and resuspended in buffer. Studies were conducted using [$^3$H]8-OH-DPAT as the radioligand. The binding assay was performed in 96 well microtiter plates in a final total volume of 250 µL of buffer. Competition experiments were performed by using 7 concentrations of unlabelled drug and a final ligand concentration of 1.5 nM . Non-specific binding was determined in the presence of 10 µM 5HT. Saturation analysis was conducted by using [$^3$H]8-OH-DPAT at concentrations ranging from 0.3–30 nM. Following a 30 minute incubation at room temperature, the reaction was terminated by the addition of ice cold buffer and rapid filtration using a M-96 Brandel Cell Harvester through a GF/B filter pre-soaked for 30 minutes in 0.5% polyethyleneimine.

A protocol simielar to that used by Cheetham et al., Neuropharmacol., 32:737, (1993), was used to determine the affinity of compounds for the serotonin transporter. Briefly, frontal cortical membranes prepared from male Sprague-Dawley rats were incubated with $^3$H-paroxetine (0.1 nM) for 60 min at 25° C. All tubes also contained either vehicle, test compound (one to eight concentrations), or a saturating concentration of fluoxetine (10 µM) to define specific binding. All reactions were terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine IC$_{50}$ values which were converted to Ki values using the method of Cheng and Prusoff, Biochem. Pharmacol., 22: 3099 (1973): Ki=IC50 ((Radioligand conc.)/(1 +KD)).

The degree of agonism/antagonism at the 5-HT$_{1A}$ receptor using [$^{35}$S]-GTPγS binding to cloned human 5HT$_{1A}$ receptors was determined as follows. The [$^{35}$S]-GTPγS binding assay was similar to that used by Lazareno and Birdsall, Br. J. Pharmacol., 109: 1120, (1993). Briefly, 5-HT$_{1A}$cloned receptor membrane fragments (as used for 5-HT$_{1A}$ receptor binding assays) were stored at –70° C. until needed. When needed, membranes were rapidly thawed, centrifuged at 40,000 xg for 10 minutes and resuspended at 4° C. for 10 minutes in assay buffer (25 mM HEPES, 3 mM MgCl$_2$, 100 mM NaCl, 1 mM EDTA, 10 uM GDP, 500 mM DTT, pH 8.0). These membranes were then incubated for 30 min at 30° C. with [$^{35}$S]GTPgS (1 nM) in the presence of vehicle, test compound (one to eight concentrations), or excess 8-OH-DPAT to define maximum agonist response. All reactions were terminated by the addition of ice cold Tris buffer followed by rapid filtration using a Tom Teche® filtration device to separate bound from free [$^{35}$S]GTPgS. Agonists produce an increase in the amount of [$^{35}$S]GTPgS bound whereas antagonists produce no increase in binding. Bound radioactivity was counted and analyzed as above.

The following assays were performed by incubating the cells with DMEM containing 25 mM HEPES, 5 mM theo-phylline and 10 µM pargyline for a period of 20 minutes at 37° C. Functional activity was assessed by treating the cells with forskolin (1 uM final concentration) followed immediately by test compound (6 concentrations) for an additional 10 min at 37° C. In separate experiments, 6 concentrations of antagonist were preincubated for 20 min prior to the addition of 10 nM 8-OH-DPAT and forskolin. The reaction was terminated by removal of the media and addition of 0.5 ml ice cold assay buffer. Plates were stored at –20° C. prior to assessment of cAMP formation by a cAMP SPA assay (Amersham).

The compounds tested correspond to those prepared in Examples 1 to 20 below. The results of the pharmacological test procedure are set forth in Table 1.

TABLE I

| Example | 5-HT$_{1A}$ (Ki, nM) | ST (K$_i$, nM, % Inh. @ .1 µM) |
| --- | --- | --- |
| 1 | 6.9 | 79 |
| 2 | 5.9 | 112 |
| 3 | 7.8 | 21 |
| 4 | 76.1 | 81 |
| 5 | 8.5 | 5.7 |
| 6 | 7.2 | 23 |
| 7 | 30.2 | 23 |
| 8 | 2.8 | 25 |
| 9 | 94.4 | 20 |
| 10 | 8.15 | 85 |
| 11 | 7.14 | 43 |
| 12 | 75.8 | 7 |
| 13 | 15.3 | 15 |
| 14 | 16.8 | 26 |
| 15 | 75.2 | 44 |
| 16 | 11.0 | 16 |
| 17 | 103.0 | 15 |
| 18 | 18.1 | 34 |
| 19 | 63.4 | 40 |
| 20 | 12.3 | 23 |

As demonstrated by the results set forth above, the compounds of the present invention are active towards 5-HT$_{1A}$ receptors and generally elevate serotonin concentrations by inhibiting 5-HT transport. Accordingly, it is believed that the present compounds would be useful in treating disorders related to defects in serotonin concentration, such as anxiety and depression.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Any of the solid carriers known to those skilled in the art may be used with the compounds of this invention. Particularly suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

Liquid carriers may be used in preparing solutions, suspensions, emulsions, syrups and elixirs of the compounds of this invention. The compounds of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmoregulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols e.g. glycols) and their derivatives and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Compositions for oral administration may be either liquid or solid composition form.

Preferably, the pharmaceutical compositions containing the compounds of this invention are in unit dosage form, e.g. as tablets or capsules. In such form, the compositions may be sub-divided in unit doses containing appropriate quantities of the present compounds. The unit dosage forms can be packaged compositions, for example, packeted powders, vials, ampoules, prefilled syringes or sachets containing liquids. Alternatively, the unit dosage form can be, for example, a capsule or tablet itself, or it can be the appropriate number of any such compositions in package form.

The therapeutically effective amount of the compounds of this invention that is administered and the dosage regimen depends on a variety of factors, including the weight, age, sex, and medical condition of the subject, the severity of the disease, the route and frequency of administration, and the specific compound employed, and thus may vary widely. However, it is believed that the pharmaceutical compositions may contain the compounds of this invention in the range of about 0.1 to about 2000 mg, preferably in the range of about 0.5 to about 500 mg and more preferably between about 1 and about 100 mg. Projected daily dosages of active compound are about 0.01 to about 100 mg/kg body weight. The daily dose can be conveniently administered two to four times per day.

The present invention may be embodied in other specific forms without departing from the spirit and essential attributes thereof and accordingly, reference should be made to the appended claims, rather than to the foregoing specification, as indicating the scope of the invention.

What is claimed is:
1. A compound of the formula

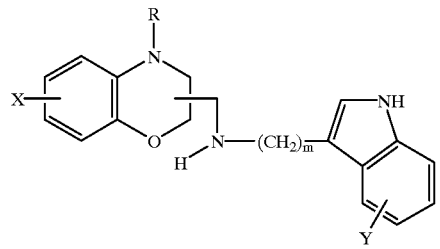

wherein:
R is hydrogen, alkyl of 1 to 6 carbon atoms, phenyl, benzyl or substituted phenyl;
X and Y are each, independently, hydrogen, halogen, cyano, or alkoxy of 1 to 6 carbon atoms; and
m is 1 to 5; or
a pharmaceutically acceptable salt thereof.

2. A compound as in claim 1, wherein R is hydrogen, cyano, or alkyl of 1 to 4 carbon atoms; X and Y are each, independently, hydrogen, halogen or cyano; and m is 2 to 4; or a pharmaceutically acceptable salt thereof.

3. The compound of claim 1, which is [(3,4)-dihydro-2H-benzo[1,4]oxazin-2-yl-methyl)]-[3-(1H-indo-3-yl)-propyl]-amine.

4. The compound of claim 1, which is [3-(1H-Indol-3-yl)-propyl]-(4-methyl-3,4-dihydro-2H-benzo [1,4]oxazin-2-yl-methyl)-amine.

5. The compound of claim 1, which is (4-Benzyl-3,4-dihydro-2H-benzo[1,4]oxazin-2-yl-methyl)-[3-(1H-indo-3-yl)-propyl]-amine.

6. The compound of claim 1, which is (4-Benzyl-3,4-dihydro-2H-benzo[1,4]oxazin-2-yl-methyl)-[3-(1H-indo-3-yl)-butyl]-amine.

7. The compound of claim 1, which is [3-(5-Fluoro-1H-indol-3-yl)-propyl]-(4-methyl-3,4-dihydro-2H-benzo[1,4] oxazin-2-yl-methyl)-amine.

8. The compound of claim 1, which is [3-(1H-Indol-3-yl)-propyl]-(4-benzyl-3,4-dihydro-2H-benzo[1,4]oxazin-2-yl-methyl)-amine.

9. The compound of claim 1, which is [3-(1H-Indol-3-yl)-propyl]-(4-phenyl-3,4-dihydro-2H-benzo[ 1 ,4]oxazin-2-yl-methyl)-amine.

10. The compound of claim 1, which is [13-(5-Fluoro-1H-indol-3-yl)-propyl]-4-isopropyl-3,4-dihydro2H-benzo [1,4]oxazin-2-yl-methyl-amine.

11. The compound of claim 1, which is [3-(1H-Indol-3-yl)-butyl]-(4-isopropyl-3,4-dihydro-2H-benzofl,4]oxazin-2-yl-methyl)-amine.

12. The comound of claim 1, which is [3-(5-Fluoro-1H-indol-3-yl)-propyl]-(4-isobutyl-3,4-dihydro-2H-benzo[1,4] oxazin-2-yl-methyl)-amine.

13. The compound of claim 1, which is [3-(5-Fluoro-1H-indol-3-yl)-propyl]-(4-phenyl-3,4-dihydro-2H-benzo[1,4] oxazin-2-yl-methyl)-amine.

14. The compound of claim 1, which is [3-(5-Fluoro-1H-indol-3-yl)-butyl]-(4-phenyl-3,4-dihydro-2H-benzo[1,4] oxazine-2-yl-methyl)-amine.

15. The compound of claim 1, which is [3-(5-Fluoro-1H-indol-3-yl)-propyl]-(4-ethyl-3 ,4-dihydro-2H-benzo[1,4] oxazin-2-yl-methyl)-amine.

16. The compound of claim 1, which is [3-(5-Fluoro-1H-indol-3-yl)-propyl]-(4-propyl-3,4-dihydro-2H-benzo[1,4] oxazine-2-yl-methyl)-amine.

17. The compound of claim 1, which is (7-Chloro-4-methyl-3,4-dihydro-2H-benzo[1,4]oxazin-2-yl-methyl)-[3-(5-fluoro-1H-indol-3-yl)-propyl]-propyl)-amine.

18. The compound of claim 1, which is (3,4-Dihydro-2H-benzo[1,4]oxazin-2-yl-methyl)-[3-(5-fluoro-1H-indol-3-yl)-propyl]-amine.

19. The compound of claim 1, which is 7-Methoxy-3,4-dihydro-2H-benzo[1,4]oxazin-2-yl-methyl-[3-(5-fluoro-1H-indol-3-yl)-propyl]-amine.

20. The compound of claim 1, which is [3-(5-Fluoro-1H-indol-3-yl)-propyl]-4-phenyl-3,4-dihydro-2H-benzo[1,4]oxazin-2-yl-methyl)amine.

21. The compound of claim 1, which is (3,4-dihydro-2H-benzo[1,4]oxazin-3-yl-methyl)-[3-(5-fluoro-1H-indol-3-yl)propyl]-amine.

22. A pharmaceutical composition comprising a compound of the formula:

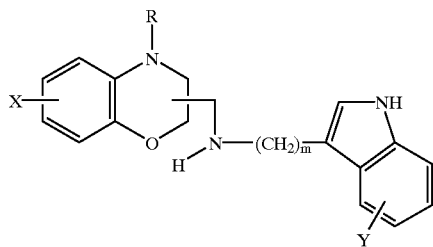

wherein:
R is hydrogen, alkyl of 1 to 6 carbon atoms, phenyl, benzyl or substituted phenyl;
X and Y are each, independently, hydrogen, halogen, cyano, or alkoxy of 1 to 6 carbon atoms; and
m is 1 to 5; or a pharmaceutically acceptable salt thereof.

23. A method for alleviating the symptoms of depression in a patient in need of treatment comprising administering to said patient an antidepressant effective amount of a compound of the formula:

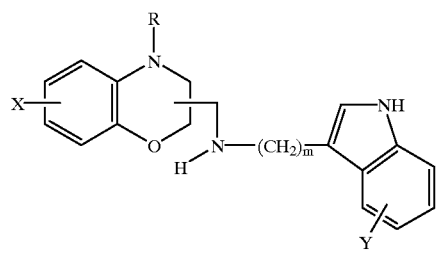

wherein:

R is hydrogen, alkyl of 1 to 6 carbon atoms, phenyl, benzyl or substituted phenyl;

X and Y are each, independently, hydrogen, halogen, cyano, or alkoxy of 1 to 6 carbon atoms; and m is 1 to5;or a pharmaceutically acceptable salt thereof.

* * * * *